(12) United States Patent
Phung et al.

(10) Patent No.: US 7,749,243 B2
(45) Date of Patent: *__Jul. 6, 2010__

(54) EMBOLUS EXTRACTOR

(75) Inventors: Mark Minh Phung, Union City, CA (US); Pete Phong Pham, Fremont, CA (US); Mehran Bashiri, San Carlos, CA (US); Beth Camins, Fremont, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1457 days.

This patent is subject to a terminal disclaimer.

(21) Appl. No.: 10/341,181

(22) Filed: Jan. 13, 2003

(65) Prior Publication Data

US 2003/0153944 A1  Aug. 14, 2003

Related U.S. Application Data

(63) Continuation-in-part of application No. 10/045,565, filed on Oct. 19, 2001, now Pat. No. 7,052,500.

(51) Int. Cl.
*A61M 29/00* (2006.01)

(52) U.S. Cl. .................................... 606/200

(58) Field of Classification Search ................ 606/113, 606/200; 600/200, 113, 114, 198, 159
See application file for complete search history.

(56) References Cited

U.S. PATENT DOCUMENTS

| | | | |
|---|---|---|---|
| 4,046,150 A | 9/1977 | Schwartz et al. | |
| 4,198,960 A | 4/1980 | Utsugi | |
| 4,347,846 A | 9/1982 | Dormia | |
| 4,873,978 A | 10/1989 | Ginsburg | |
| 4,998,539 A | 3/1991 | Delsanti | |
| 5,152,777 A | 10/1992 | Goldberg et al. | |
| 5,171,233 A | 12/1992 | Amplatz et al. | |
| 5,192,286 A * | 3/1993 | Phan et al. | 606/113 |
| 5,234,458 A | 8/1993 | Metais | |
| 5,330,482 A * | 7/1994 | Gibbs et al. | 606/113 |
| 5,486,183 A | 1/1996 | Middleman et al. | |
| 5,496,330 A | 3/1996 | Bates et al. | |
| 5,509,923 A | 4/1996 | Middleman et al. | |
| 5,527,326 A * | 6/1996 | Hermann et al. | 606/159 |
| 5,601,572 A | 2/1997 | Middleman et al. | |
| 5,662,671 A | 9/1997 | Barbut et al. | |
| 5,695,518 A | 12/1997 | Laerum | |
| 5,709,704 A | 1/1998 | Nott et al. | |
| 5,720,754 A | 2/1998 | Middleman et al. | |
| 5,820,628 A | 10/1998 | Middleman et al. | |

(Continued)

FOREIGN PATENT DOCUMENTS

EP  0 418 677 A1  3/1991

(Continued)

*Primary Examiner*—Anhtuan T Nguyen
*Assistant Examiner*—Tuan V Nguyen
(74) *Attorney, Agent, or Firm*—Crompton, Seager & Tufte LLC

(57) ABSTRACT

An embolus extractor including elongate shaft having a proximal end and a distal end. The embolus extractor may include primary struts coupled to the distal end of the shaft. The struts may define a proximally disposed mouth. Additional secondary struts may be coupled along the elongate shaft to enhance the thrombus containing ability of the embolus extractor.

30 Claims, 9 Drawing Sheets

U.S. PATENT DOCUMENTS

| | | | |
|---|---|---|---|
| 5,895,398 A * | 4/1999 | Wensel et al. | 606/159 |
| 5,904,690 A | 5/1999 | Middleman et al. | |
| 5,941,869 A * | 8/1999 | Patterson et al. | 604/508 |
| 6,053,932 A | 4/2000 | Daniel et al. | |
| 6,059,814 A * | 5/2000 | Ladd | 606/200 |
| 6,146,396 A | 11/2000 | Kónya et al. | |
| 6,168,603 B1 | 1/2001 | Leslie et al. | |
| 6,203,561 B1 | 3/2001 | Ramee et al. | |
| 6,402,771 B1 | 6/2002 | Palmer et al. | |
| 6,436,121 B1 | 8/2002 | Blom | |
| 6,468,291 B2 * | 10/2002 | Bates et al. | 606/200 |
| 6,511,492 B1 * | 1/2003 | Rosenbluth et al. | 606/159 |
| 6,749,619 B2 * | 6/2004 | Ouriel et al. | 606/200 |
| 6,936,059 B2 * | 8/2005 | Belef | 606/200 |
| 2001/0031981 A1 * | 10/2001 | Evans et al. | 606/200 |
| 2002/0010487 A1 | 1/2002 | Evans et al. | |
| 2002/0143361 A1 | 10/2002 | Douk et al. | |
| 2003/0078605 A1 * | 4/2003 | Bashiri et al. | 606/159 |
| 2004/0138692 A1 * | 7/2004 | Phung et al. | 606/200 |

FOREIGN PATENT DOCUMENTS

| | | |
|---|---|---|
| EP | 0 820 729 A1 | 1/1998 |
| WO | WO 03/034929 A1 | 5/2003 |

* cited by examiner

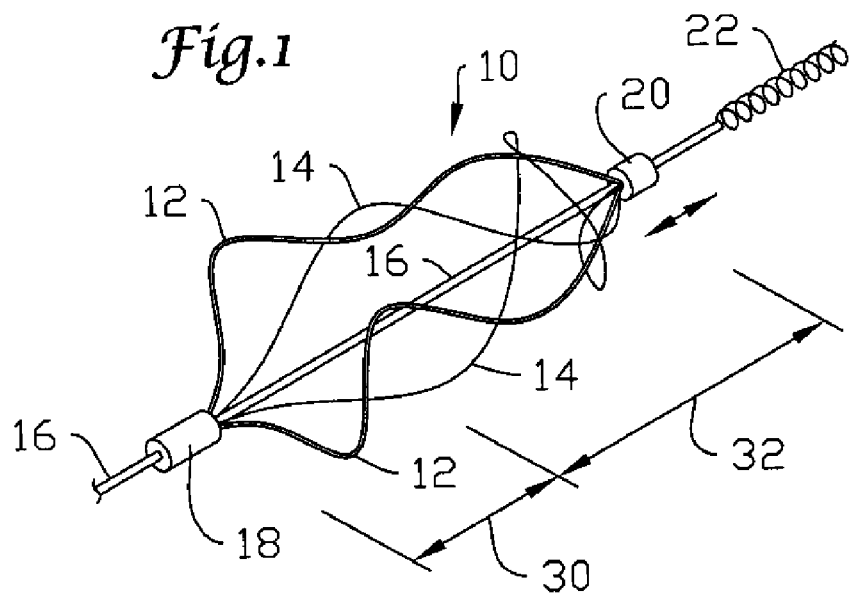
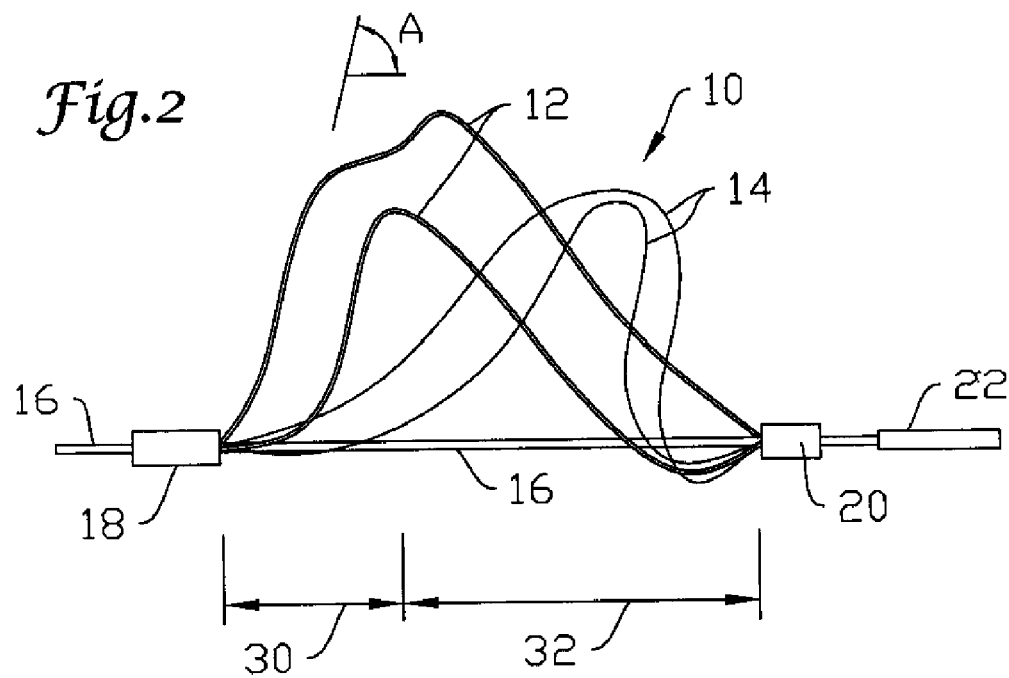

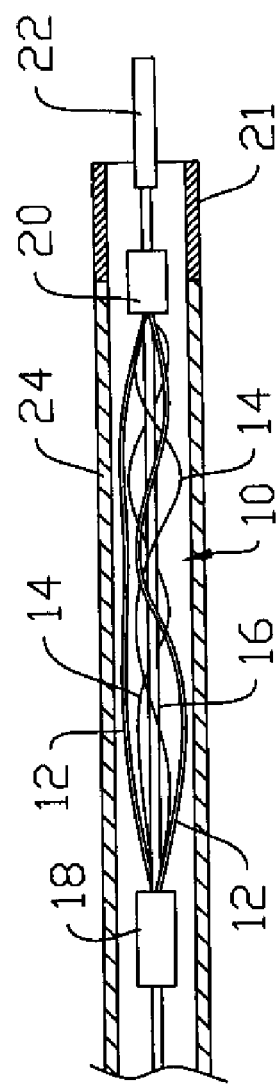
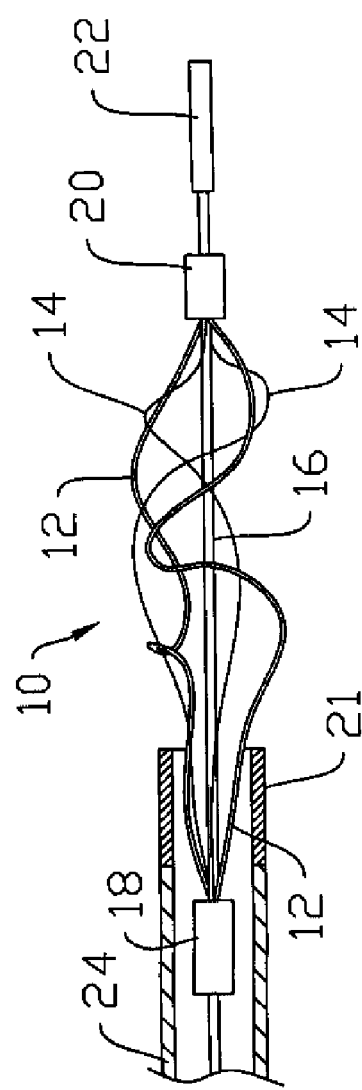

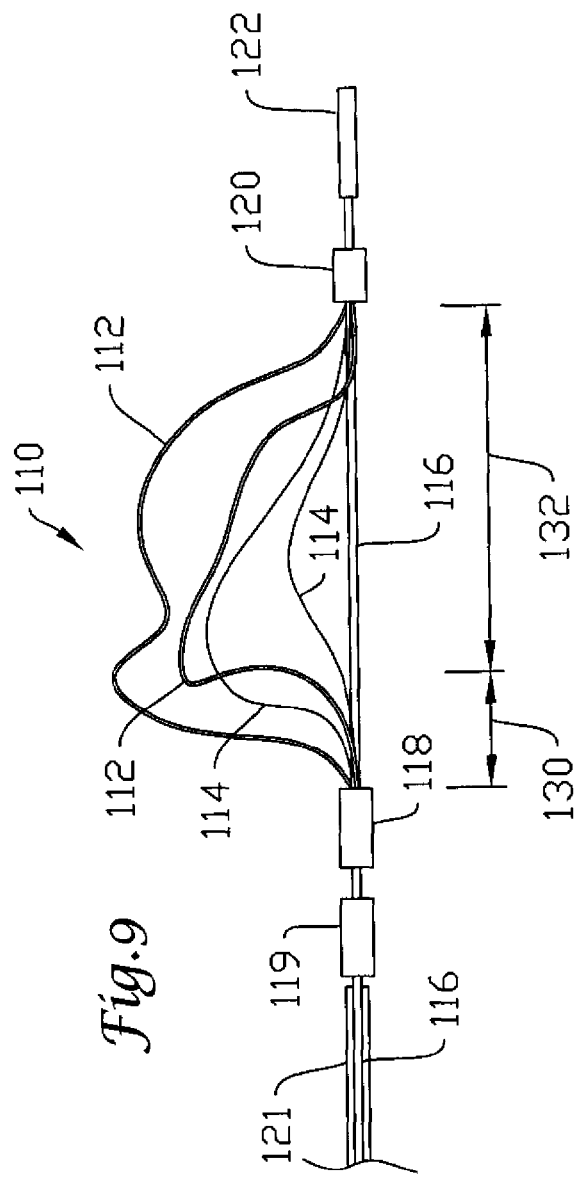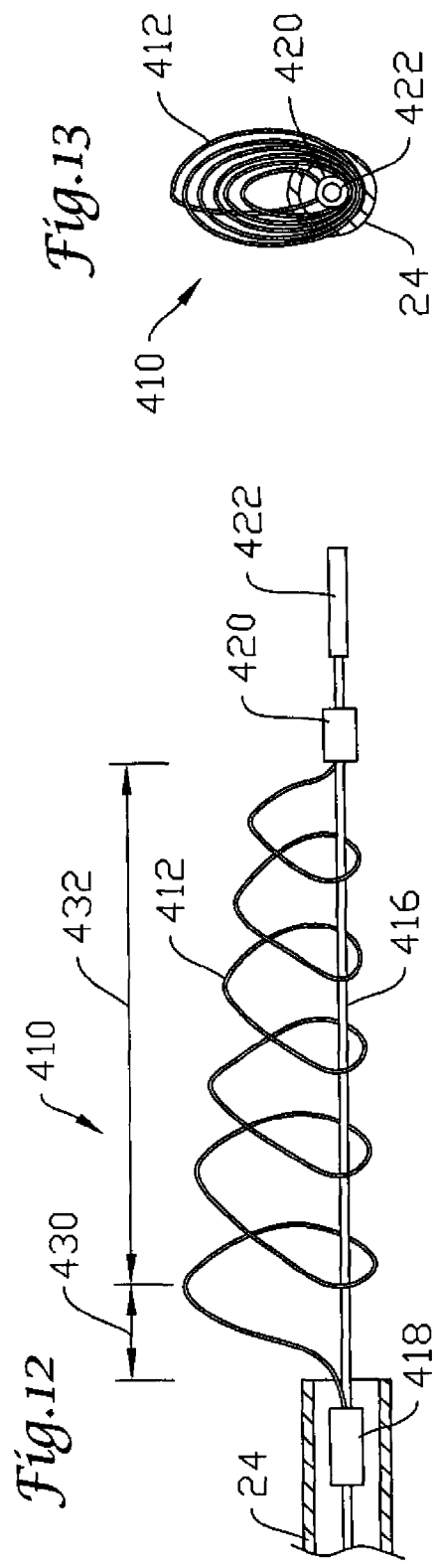

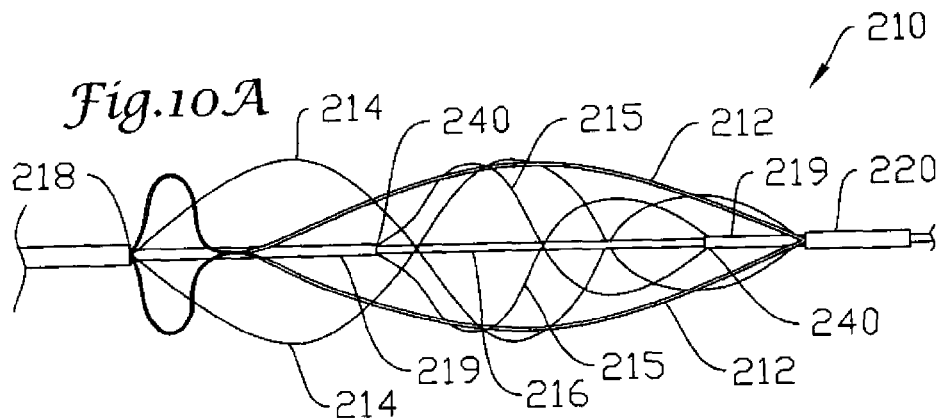
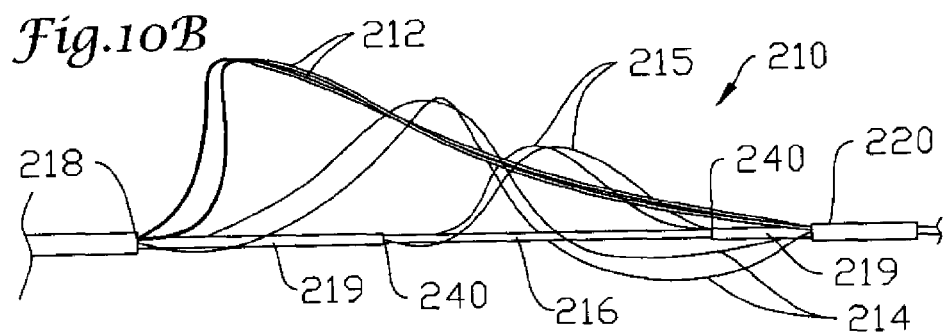
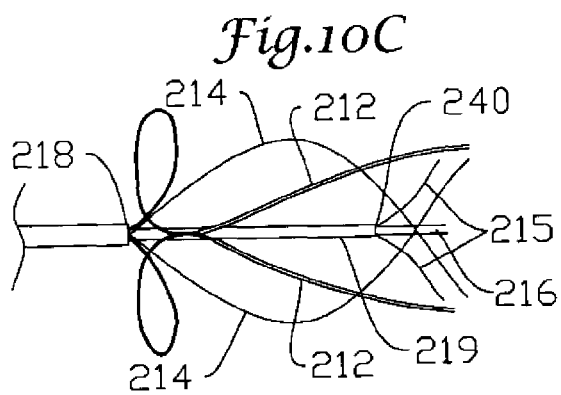 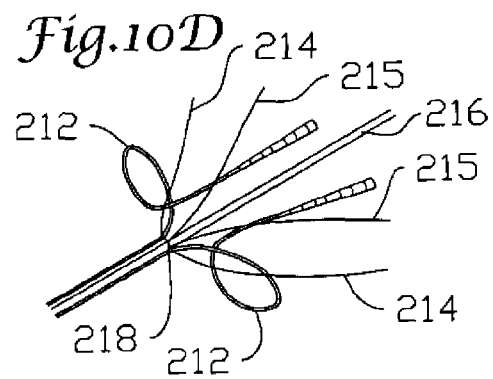
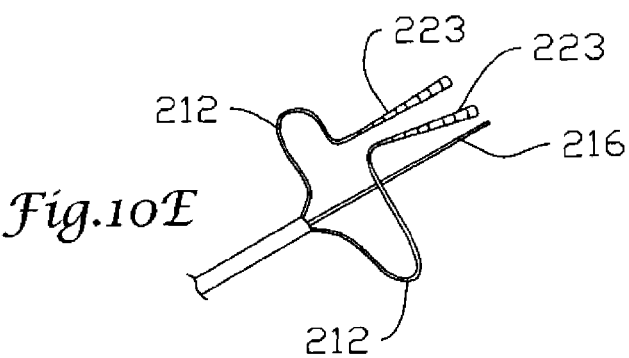

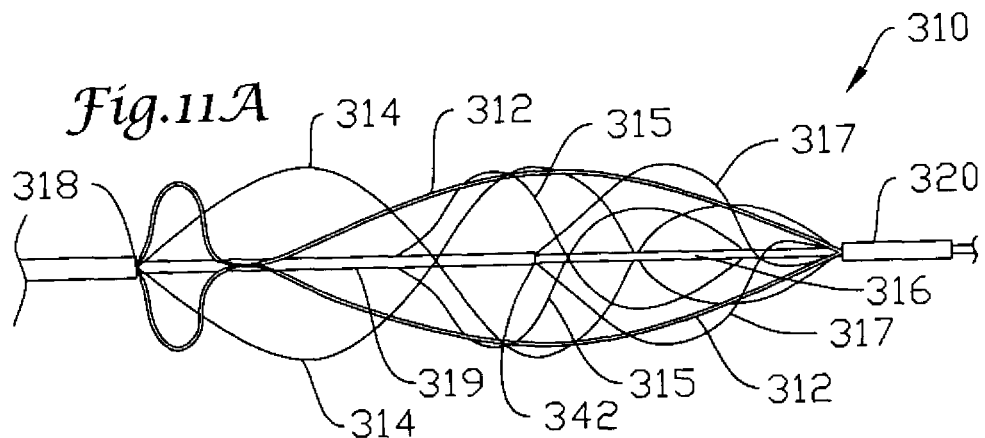
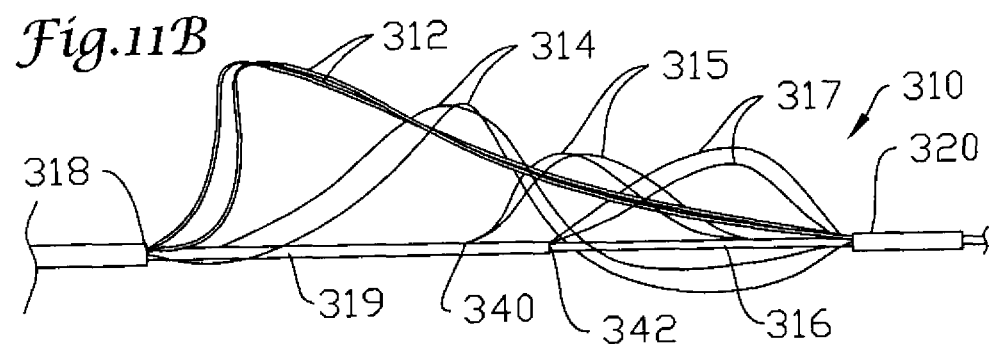
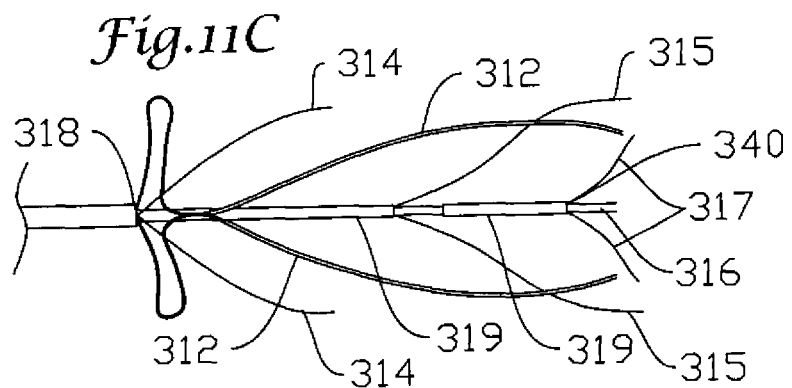
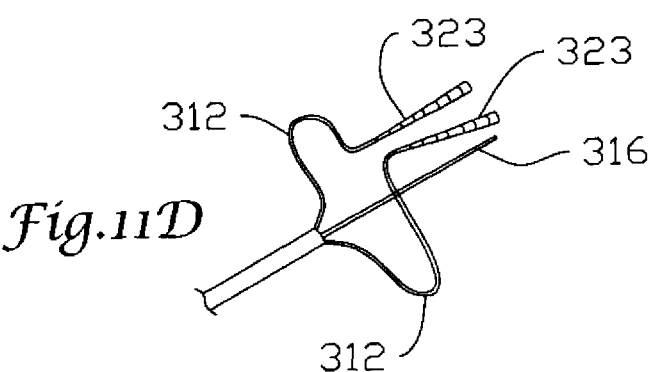

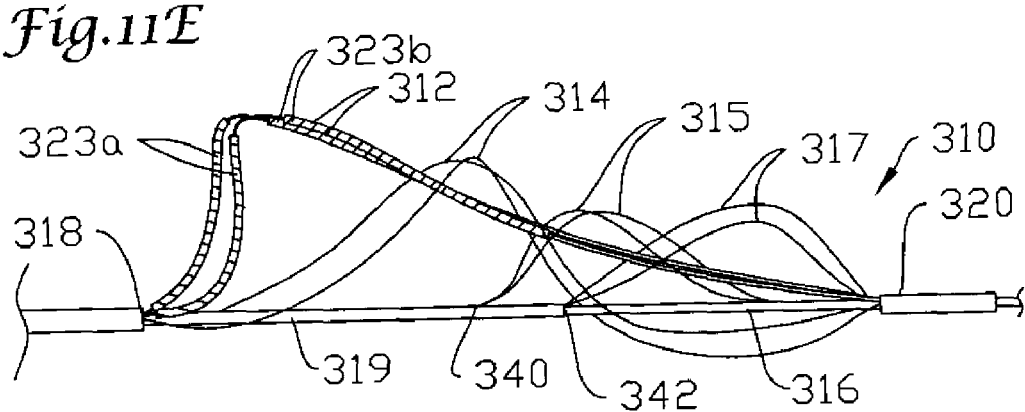
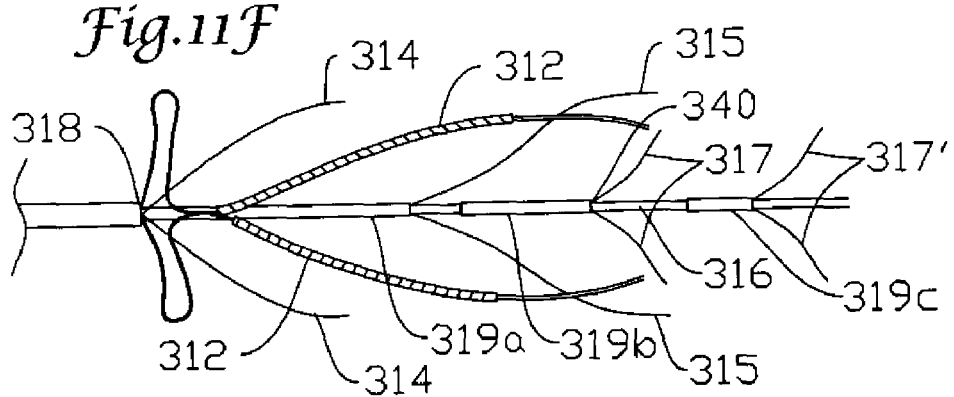
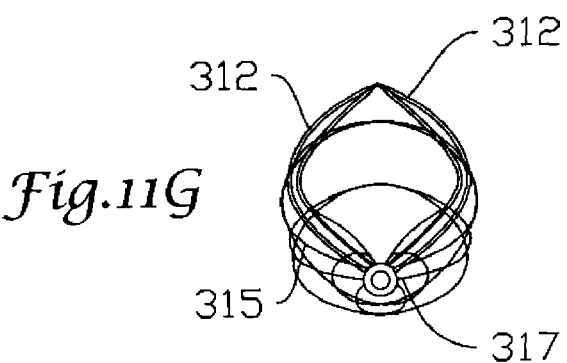

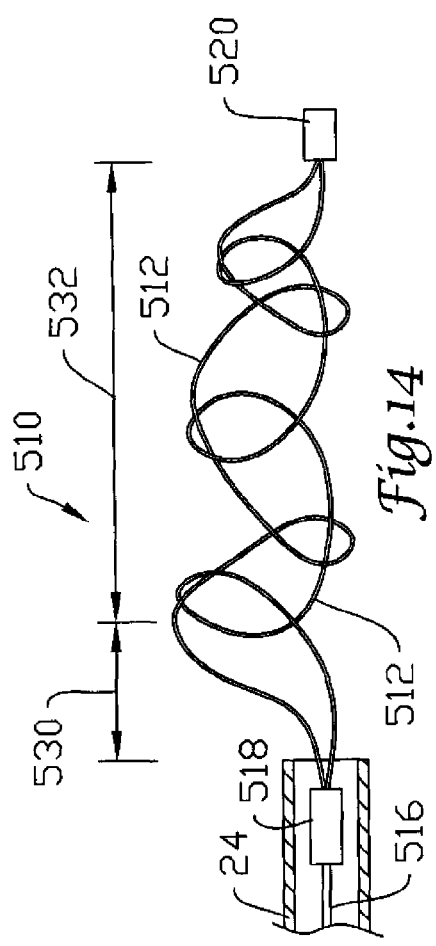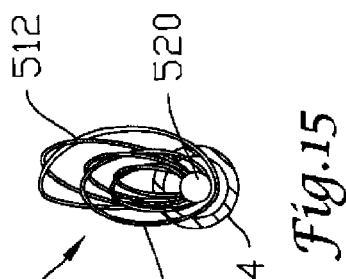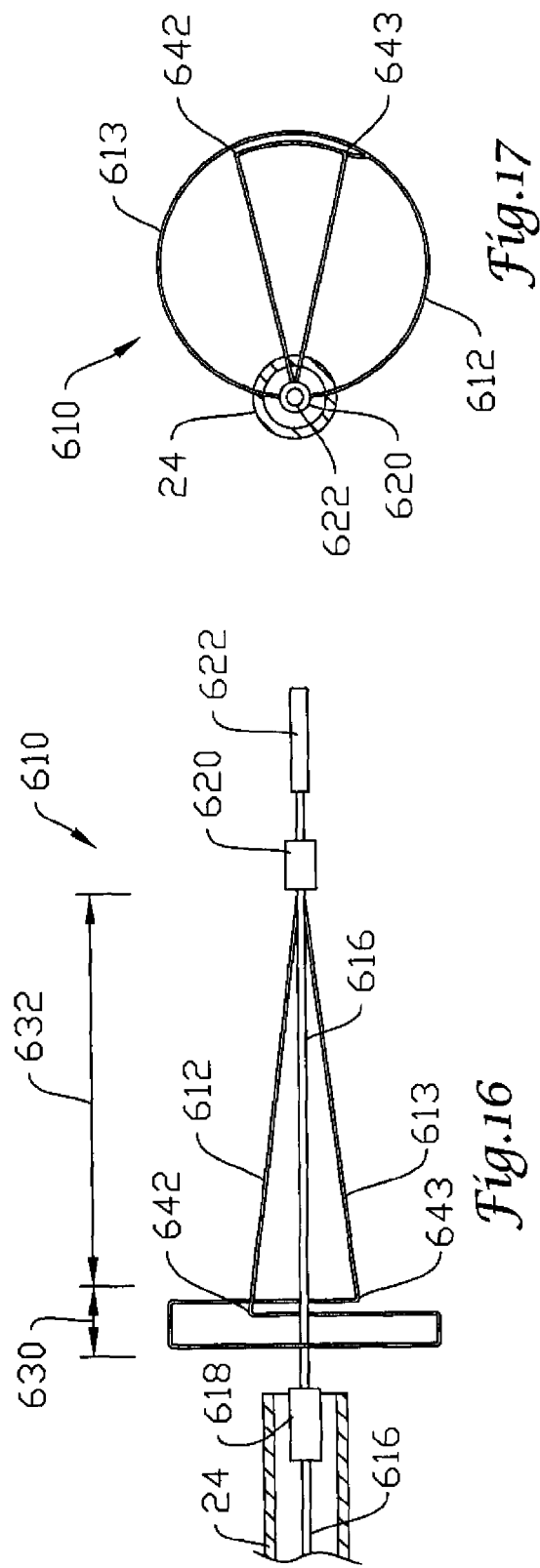

EMBOLUS EXTRACTOR

This application is a Continuation-In-Part of application Ser. No. 10/045,565, filed on Oct. 19, 2001 now U.S. Pat. No. 7,052,500.

BACKGROUND OF THE INVENTION

The present invention pertains generally to emboli collection and removal.

Blood thrombus, may form a clot in a patient's vasculature. Sometimes such clots are harmlessly dissolved in the blood stream. At other times, however, such clots may lodge in a blood vessel where they can partially or completely occlude the flow of blood. If the partially or completely occluded vessel feeds blood to sensitive tissue such as, the brain, lungs or heart, for example, serious tissue damage may result.

When symptoms of an occlusion are apparent, such as an occlusion resulting in a stroke, immediate action should be taken to reduce or eliminate resultant tissue damage. One approach is to treat a patient with clot dissolving drugs. These drugs, however, do not immediately dissolve the clot and may have harmful side effects. Thus, it may be desirable to physically remove the clot from the patient.

SUMMARY OF THE INVENTION

The present invention pertains to an improved clot or embolus extractor device and method for removing an embolus such as a clot from a vasculature. Various embodiments of the claimed invention are possible, examples of these embodiments will briefly be described herein and in more detail below in the detailed description of the invention. One embodiment of an embolus extractor in accordance with the invention includes two struts coupled to the distal end of an elongate shaft. In a first collapsed position, the struts are generally disposed parallel to the elongate shaft. In a second expanded position, the proximal end of the struts defines a generally circular mouth disposed at approximately 90° to the length of the elongate shaft. The portion of the struts extending distally of the mouth defines a generally tapered, for example, cylindrical body with a conical tip. With such a configuration, an emboli mass, such as a cylindrical thrombus may be contained by the embolus extractor.

One embodiment of an embolus extractor in accordance with the present invention includes an elongate shaft having a proximal end and a distal end. The proximal ends and distal ends of primary struts are coupled to the shaft and allow rotation of the struts around the shaft. A sleeve may be used to slidably couple the distal ends of the struts to the shaft. A sleeve may also be used to slidably couple the proximal ends of the struts to the shaft. The struts can be disposed in a first position and a second position.

In the first position, the distal ends and the proximal ends of the struts are spaced at a first distance. In the second position, the distal ends and the proximal ends of the struts are spaced at a second distance, which is less than the first distance.

In the first position, the struts can be disposed generally parallel and adjacent to the shaft. In the second position, a proximal portion of the first and second struts can define a generally circular mouth. In the second position, the portion of the struts extending generally distally from the mouth can define a generally distally tapering body. The proximal portion of the struts forming the mouth can extend from the shaft at 45° to 90° to the length of the shaft. This angle could also be between 60° and 90° or between 80° and 90°.

The struts can include a shaped memory material, such as a NiTi alloy. Additional struts can be added to the embolus extractor to enhance the thrombus containing ability of the embolus extractor. These struts may have a smaller cross sectional diameter than the primary struts, or they may be substantially the same diameter. These secondary struts may be coupled at the same locations as the primary struts along the elongate shaft, or they may be coupled at different positions located distally of the proximal end of the primary struts using, for example, additional sleeves.

In accordance with the present invention, an embolus extractor can be advanced through a patient's vasculature in a first compressed position, distally beyond a clot. The embolus extractor can then be deployed in a second expanded position, then drawn proximally to a second compressed position to capture, contain and remove the thrombus to a larger diameter vessel or from the body.

BRIEF DESCRIPTION OF THE DRAWINGS

FIG. 1 is a prospective view of a first embodiment of an embolus extractor.

FIG. 2 is a side view of the embolus extractor of FIG. 1.

FIG. 3 is a cross sectional view of a micro catheter containing the embolus extractor of FIG. 1.

FIG. 4 is a cross sectional view of the micro catheter of FIG. 2 showing the embolus extractor partially disposed from the micro catheter.

FIG. 9 is a side view of an alternate embodiment of an embolus extractor.

FIG. 10A is a top view of another alternate embodiment of an embolus extractor having six struts coupled along the shaft.

FIG. 10B is a side view of the embolus extractor of FIG. 10A.

FIG. 10C is bottom view of the embolus extractor of FIG. 10A.

FIG. 10D is an enlarged view of the embolus extractor of FIG. 10A.

FIG. 10E is an enlarged view of the embolus extractor of FIG. 10A.

FIG. 11A is a top view of another alternate embodiment of an embolus extractor having eight struts coupled along the shaft.

FIG. 11B is a side view of the embolus extractor of FIG. 11A.

FIG. 11C is bottom view of the embolus extractor of FIG. 11A.

FIG. 11D is an enlarged view of the embolus extractor of FIG. 11A.

FIG. 11E is a top view of an alternate embodiment of an embolus extractor having additional struts.

FIG. 11F is a side view of the embolus extractor of FIG. 11E.

FIG. 11G is an end view of the embolus extractor of FIG. 11E.

FIG. 12 is a side view of yet an alternate embodiment of an embolus extractor.

FIG. 13 is a distal end view of the embolus extractor of FIG. 12.

FIG. 14 is a side view of yet an alternate embodiment of an embolus extractor.

FIG. 15 is a distal end view of the embolus extractor of FIG. 14.

FIG. 16 is a top view of yet another alternate embodiment of an embolus extractor.

FIG. 17 is a distal end view of the embolus extractor of FIG. 16.

DETAILED DESCRIPTION

Figure 5:
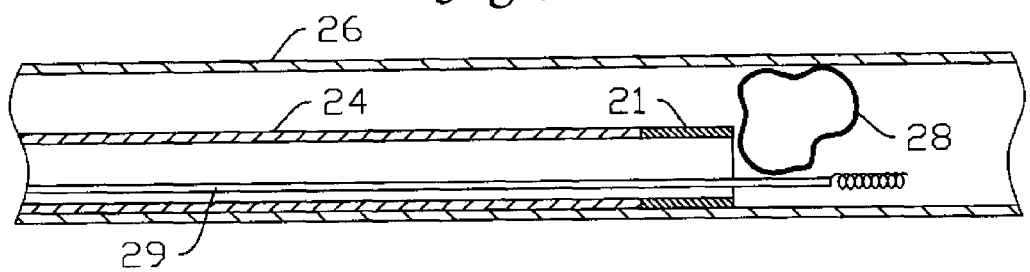
FIG. 5 is a cross sectional view of a vessel including a clot and a micro guidewire disposed in a micro catheter positioned by the clot.

Referring now to the Figures, wherein like referenced numerals refer like elements throughout the several views, FIG. 1 is a perspective view of an embolus extractor 10. Embolus extractor 10 includes first and second primary struts 12 and first and second secondary struts 14 coupled to an elongate shaft 16. Struts 12 and 14 can be coupled to shaft 16 at their proximal ends by a sleeve 18 and at their distal ends by a sleeve 20. For example, a spring tip 22 can be disposed at the distal end of shaft 16. Spring tip 22 can be selectively shaped by a physician to guide embolus extractor 10 into micro vessels and stabilize embolus extractor 10 after deployment. Alternately a radiopaque polymer can be used rather than a spring.

Struts 12 as shown in FIG. 1 are disposed in an expanded or delivered position. In this position, a proximal portion 30 extends generally perpendicularly to the length of shaft 16 to form a generally circular mouth. A distal portion 32 of struts 12 extending distally of the mouth generally tapers distally to form a distally tapered body having, for example, a generally conical distal shape. Struts 14 transverse the tapered body to enhance the clot catching and holding ability of embolus extractor 10. Struts 12 and 14 can be made from various materials including shaped memory metals, such as NiTi alloys. Secondary struts 14 may have a smaller diameter or transverse cross sectional area than primary struts 12.

Elongate shaft 16 can be formed from a material similar to those used for making guide wires, such as plastic polymers, stainless steel, NiTi alloy or other suitable material. Sleeve 18 can be formed from a wire coil. Adhesive, solder or the like may be applied to fixally connect the proximal ends of struts 12 and 14 and sleeve 18 to shaft 16 or the proximal bushing. Sleeve 20 can also be formed from a wire coil. Adhesive, solder or the like can be used to connect struts 12 and 14 to sleeve 20. If struts 12 and 14, are connected to each other, but not fixally connected to shaft 16, sleeve 20 can slide along shaft 16. Both sleeves 18 and 20 can include a radiopaque material. Struts 12 and 14 can also include radiopaque material to visualize their deployed shape.

FIG. 2 is a side view of embolus extractor 10 of FIG. 1. In FIG. 2 embolus extractor 10 is also shown in the expanded or deployed position. Proximal portion 30 of struts 12 defining the mouth is shown disposed at Angle A relative to the length of shaft 16. Angle A can be approximately 90°, between 45° and 90°, between 60° and 90°, or between 80° and 90°. It should be understood that, although Angle A is shown as the angle between the distal end of shaft 16 and proximal portion 30 of struts 12, Angle A can also be the angle between portion 30 of struts 12 and the portion of shaft 16 proximal struts 12. Since each strut 12 defining the generally circular mouth can move independently, the size of the mouth opening can vary. For example, in relatively small vessels, struts 12 can move closer together to create a smaller mouth; whereas in larger vessels, struts 12 can expand to create a larger mouth. If for example, NiTi alloy is used to form struts 12 and 14, struts 12 and 14 can have a preset expanded shape.

The length of shaft 16 and the size of the various elements of embolus extractor 10 can be selected with respect to the location in a patient's vasculature to be accessed. For example, if a patient's cerebral arteries are to be accessed from a femoral approach, the length of shaft 16 should be sized accordingly. The diameter of the generally circular mouth from the proximal portion 30 of struts 12 can be sized to atraumatically engage the wall of the vessel in which it is deployed. The number of primary and secondary struts may be increased or decreased depending on the size of the vessel and the characteristics of the clot. Also, the position of the primary and secondary struts may be varied along the elongate shaft as necessary.

FIG. 3 is a cross sectional view of a micro catheter 24 for embolus extractor 10. Micro catheter 24 can have a radiopaque marker tip 21. Tip 21 can be made from, for example, a platinum band or a polymer loaded with a radiopaque material. As shown in FIG. 3, embolus extractor 10 is disposed in a collapsed or delivery position. In this position, sleeve 20 slides distally along shaft 16 to allow struts 12 and 14 to be compressed within micro catheter 24 and be disposed generally parallel to shaft 16. FIG. 4 is a cross sectional view of micro catheter 24 wherein embolus extractor 10 is disposed in part within micro catheter 24 and in part distally of micro catheter 24. Struts 12 and 14 can be biased to self expand as micro catheter 24 is removed.

FIG. 5 is a cross sectional view of a blood vessel 26 which may be, for example, a cerebral artery. A clot 28, including thrombus, is shown occluding vessel 26. A micro guidewire 29 has been advanced distally of clot 28. Micro catheter 24 will then also be advanced distally of clot 28.

Figure 6:
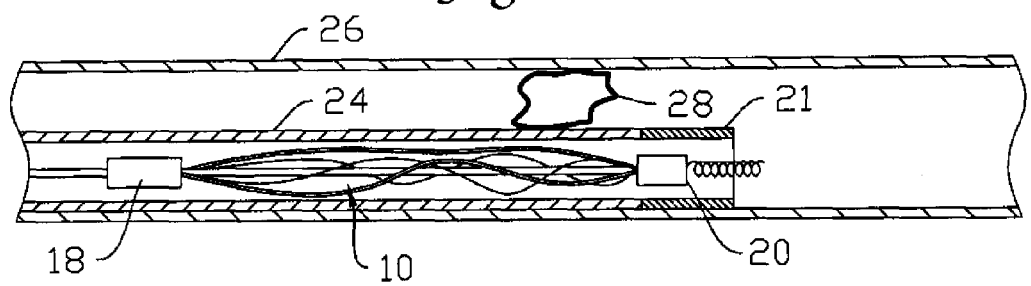
FIG. 6 is a cross sectional view of the vessel of FIG. 5 showing the micro catheter and embolus extractor traversing the clot.

As shown in FIG. 6, micro catheter 24 has been advanced distally of clot 28. Micro guidewire 29 has been removed proximally. Embolus extractor 10 has been placed in micro catheter 24 by an introducer sheath (not shown) at the proximal end of micro catheter 24.

Figure 7:
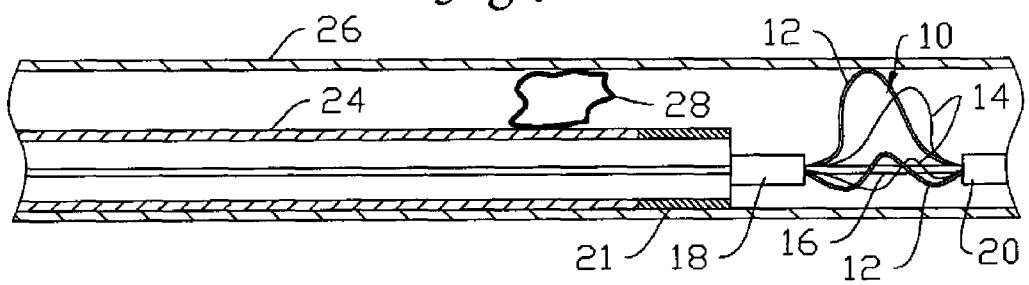
FIG. 7 is a cross sectional view of the vessel of FIG. 5 showing the embolus extractor deployed distally of the clot.

As shown in FIG. 7, once micro catheter 24 and embolus extractor 10 are advanced at least in part distally of clot 28, embolus extractor 10 may be deployed by further advancing embolus extractor 10 relative to micro catheter 24 such that struts 14 and 12 are allowed to expand. Alternately, micro catheter 24 can be retracted proximally relative to embolus extractor 10 to allow struts 12 and 14 to expand.

Figure 8:
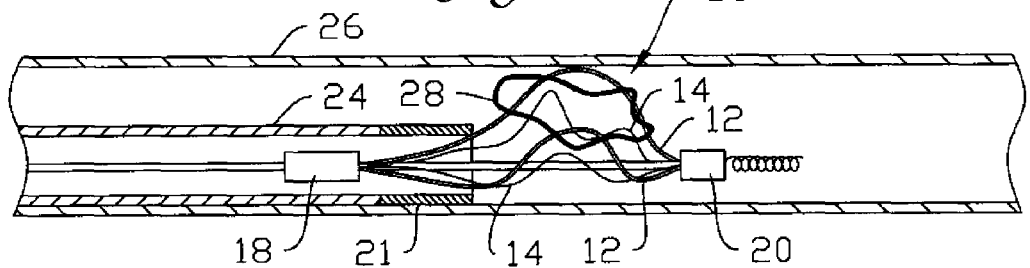
FIG. 8 is a cross sectional view of the vessel of FIG. 5 showing the clot captured by the embolus extractor and the extractor puller locked at the tip of the micro catheter.

As shown in FIG. 8, embolus extractor 10 can then be drawn proximally such that struts 14 and 12 engage and capture clot 28. If struts 12 have been configured such that the proximal mouth engages the wall of vessel 26, the mouth portion can act as a separator to release clot 28 from the vessel wall. After clot 28 has been captured by embolus extractor 10, the profile of struts 12 and 14 can be reduced by placing struts 12 and 14, at least in part, in micro catheter. If sleeve 18 and tip 21 are radiopaque the relative distance that embolus extractor 10 is withdrawn within micro catheter 24 can be observed by fluroscopy. Clot 28, embolus extractor 10 and micro catheter 24 can then be removed proximally by way of, for example, a guide catheter (not shown).

FIG. 9 is a side view of an alternate embodiment of an embolus extractor 110. Embolus extractor 110 can be made from materials, and in an expanded position used in a manner similar to embolus extractor 10. It includes primary struts 112 and secondary struts 114. Primary struts 112 and secondary struts 114 are coupled to elongate shaft 116 at their proximal ends by sleeve 118 and at their distal ends by sleeve 120. In this embodiment, however, both sleeves 120 and 118 are free to slide along shaft 116. In an alternate embodiment, sleeve 118 or 120 is fixed relative to shaft 116, or both sleeves 118 and 120 are fixed relative to shaft 116. Proximal movement, however, can be limited by a stop 119 fastened to elongate shaft 116. Distal movement can be limited by spring tip 122. Alternately, a radiopaque polymer can be used rather than a spring. Like shaft 16, shaft 116 can be formed from a wire.

Shaft 116 can include a polymer coating 121 to improve collapse and repositioning processes of the device. Coating 121 can be polymer tetrafluorine ethylene (PTFE) or other suitable material. Such a coating could be used on any of the shafts described herein.

A proximal end 130 of struts 112 defines a generally circular mouth. A distal portion 132 of struts 112 can define a generally tapered body portion. The mouth portion of embolus extractor 110 can be disposed at an Angle A to shaft 116 as described above with respect to Angle A and embolus extractor 10.

FIG. 10A is a top view of an alternate embodiment of an embolus extractor 210. Embolus extractor 210 can be made from materials, and in an expanded position used in a manner similar to embolus extractor 10 and made from similar materials. Embolus extractor 210 includes primary struts 212 and first and second secondary struts 214 coupled to elongate shaft 216 at proximal coupling point 218 and distal sleeve 220. It also includes third and fourth secondary struts 215 having proximal ends and distal ends coupled to the shaft 216 at intermediate coupling points 240 by sleeves 219. Sleeves 219 may be made of a wire coil and slidably disposed along elongate shaft 216. Sleeves 219 may be made of radiopaque material.

FIG. 10B is a side view of embolus extractor 210 of FIG. 10A. The arrangement of secondary struts 214, 215 along elongate shaft 216 and the location of the intermediate coupling points 240 are shown.

FIG. 10C is an enlarged view of the embolus extractor 210 of FIG. 10A. Sleeve 219, used to couple secondary struts 215 to elongate shaft 216, can be seen located distally of primary strut 212 coupling point 218.

FIG. 10D is an enlarged view of an alternate embodiment of embolus extractor 210 of FIG. 10A. In this embodiment, secondary struts 214, 215 are both coupled to elongate shaft 212 at proximal coupling point 218.

FIG. 10E is an enlarged view of embolus extractor 210 of FIG. 10A. Radiopaque markers 223, preferably made of a wire coil, can be seen attached to struts 212.

FIG. 11A is a top view of an alternate embodiment of an embolus extractor 310. Embolus extractor 310 can be made of materials, and in an expanded position used in a manner similar to embolus extractor 10 and made from similar materials. Embolus extractor includes fifth and sixth secondary struts 317 coupled to the elongate shaft 316 with a sleeve 319 at second intermediate coupling point 342 distal of first intermediate coupling point 340. Although this embodiment shows eight struts coupled along the elongate shaft 316, it is within the scope of the invention to include additional struts as necessary.

FIG. 11B is a side view of embolus extractor 310 of FIG. 11A. The arrangement of secondary struts 314, 315, 317 along elongate shaft 316 and the location of intermediate coupling points 240, 242 are shown.

FIG. 11C is an enlarged view of embolus extractor 310 of FIG. 11A. Sleeves 319 used to couple the second pair of secondary struts 315 and third pair of secondary struts 317 to other elongate shafts 319 at intermediate coupling points 340 can be seen located distally of primary strut 212 coupling point 218.

FIG. 11D is an enlarged view of embolus extractor 310 of FIG. 11A. Radiopaque markers 323, preferably made of a wire coil, can be seen attached to struts 312.

FIGS. 11E and 11F depict an enlarged view of an alternate embodiment of embolus extractor 310'. Radiopaque markers (one pair of 223A and one pair of 223B) preferably made of a wire coil, can be seen attached to struts 312. Also shown, sleeve 319A may be used to couple the second pair of secondary struts 315' along the shaft 316. Additional secondary struts 317' are shown extending from the sleeves 319B and 319C at intermediate coupling points 350 located distally of primary struts 312' and continuing to distal sleeve 320. The sleeves 319B and 319C may be located at the distal end of the radiopaque marker 323A coupling point. FIG. 11G shows the arrangement of struts of embolus extractor 310' as seen looking from the distal end of the embolus extractor.

FIG. 12 describes yet another embodiment of embolus extractor 410 in an expanded position. Embolus extractor 410 can be made from materials, and used in a way similar to that described above with respect to embolus extractor 10. Embolus extractor 410 includes a generally helical strut 412 coupled to an elongate shaft 416 at its proximal end by sleeve 418, and its distal end by sleeve 420. Sleeve 418 or sleeve 420 can be slidable along shaft 416. If both sleeve 418 and sleeve 420 are slidable along shaft 416, it may be desirable in addition to providing spring tip 422, to provide a proximal stop (not shown) proximal sleeve 418. Alternately, a radiopaque polymer can be used rather than a spring. In an alternate embodiment, sleeve 418 or sleeve 420 can be fixed relative to shaft 416, or both sleeves 418 and 420 can be fixed relative to shaft 416.

A proximal portion 430 of strut 412 can form a generally circular mouth. Distal portion 432 of strut 412 can taper distally to form a tapered body. Portion 430 of strut 412 can be disposed at an Angle A to elongate shaft 416 as described above with respect to Angle A of embolus extractor 10.

FIG. 13 is a distal end view of embolus extractor 410 of FIG. 12. The generally circular mouth and tapering body of strut 412 can be seen in FIG. 13.

FIG. 14 is a side view of yet another alternate embodiment of an embolus extractor 510 in an expanded position. Embolus extractor 510 can be made from materials, and used in a manner similar to that described above with respect to embolus extractor 10. Embolus extractor 510 includes primary struts 512. Struts 512 can be connected at their proximal ends by sleeve 518 to an elongate shaft 516. Struts 512 can be coupled together at their distal ends by sleeve 520.

Proximal end 530 of struts 512 can define a generally circular mouth. Distal portion 532 of struts 512 can taper distally to form a distal body portion. Portion 530 of struts 512 can be disposed at an Angle A to elongate shaft 516 as described above with respect to embolus extractor 10.

FIG. 15 is a distal end view of embolus extractor 510 of FIG. 14. The generally circular mouth and tapered body portion of embolus extractor 510 can be seen in FIG. 15.

FIG. 16 is a top view of yet another alternate embodiment of an embolus extractor 610 in an expanded position. Embolus extractor 610 can be made from materials similar to, and used in a manner similar to embolus extractor 10 as described above. Embolus extractor 610 includes primary struts 612 and 613. Primary struts 612 and 613 can be coupled to an elongate shaft 616 at their proximal ends by sleeve 618 and at their distal ends by sleeve 620. Sleeve 618 or sleeve 620 can be slidable along shaft 616. It may be desirable, however, if both sleeve 618 and 620 are slidable along shaft 616 to provide a stop proximal sleeve 618. A distal spring tip 622 can act as a distal stop. Alternately, a radiopaque polymer can be used rather than a spring. Proximal portion 630 of primary struts 612 and 613 can form a generally circular mouth. Distal portion 632 of primary struts 612 and 613 can taper distally to form a generally tapered body. A transition between proximal portion 630 and distal portion 632 can occur at bend 642 along primary strut 612 and at bend 643 along primary strut 613.

FIG. 17 is a distal end view of embolus extractor 610. The circular mouth and tapered body defined by struts 612 and 613 can be seen in FIG. 17. Additionally, it can be seen that strut 613 in part overlaps strut 612.

Figure 18:
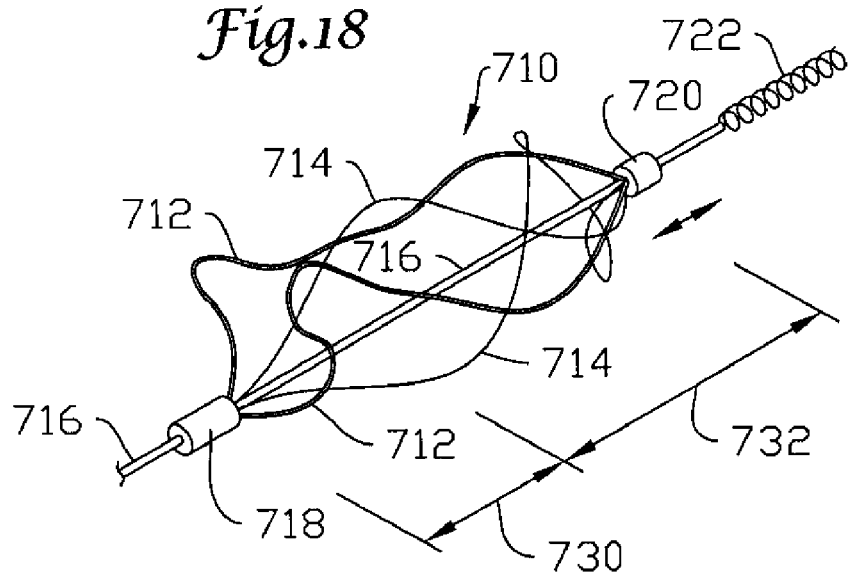
FIG. 18 is a perspective view of an embodiment of an embolus extractor.
Figure 19:
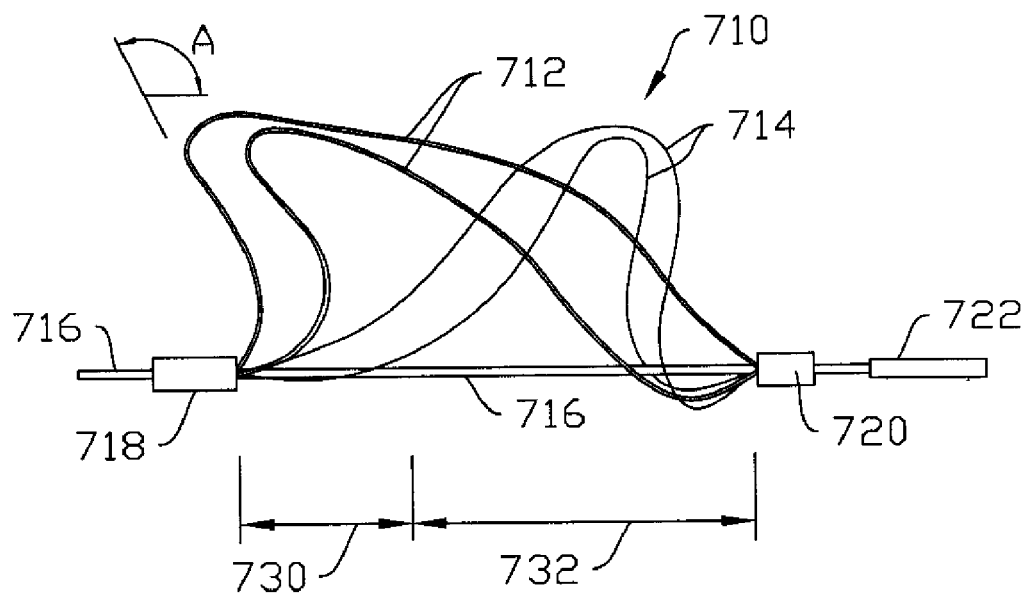
FIG. 19 is a side view of the embolus extractor of FIG. 18.

FIG. 18 is a perspective view of an embolus extractor 710 similar to embolus extractor 10 of FIG. 1. Embolus extractor 710 includes first and second primary struts 712 and first and second secondary struts 714 coupled to an elongate shaft 716. Struts 712 and 714 may be coupled to shaft 716 by sleeves 718 and 720. A spring tip 722 can be disposed at the distal end of shaft 716. A proximal portion 730 of primary struts 712 defines a generally circular mouth. As can be seen in FIG. 19, as shown by angle A, portion 370 of strut 712 extend generally proximally from shaft 716. Angle A can be for example, the same angles as those identified above for angle A of embolus extractor 10. Struts 712 also include a distal portion 732.

It should be understood that this disclosure is, in many respects, only illustrative. Changes may be made in details, particularly in matters of shape, size, and arrangement of steps without exceeding the scope of the invention. The inventor's scope is, of course, defined in the language in which the pending claims are expressed.

We claim:

1. An embolus extractor, comprising:
    an elongate shaft having a proximal end and a distal end;
        a plurality of primary struts, each strut having a proximal end and a distal end coupled to the distal end of the shaft;
        the primary struts having a first position and a second position, wherein in the first position, the distal ends and the proximal ends of the primary struts are spaced at a first distance, and in the second position the distal ends and the proximal ends of the struts are spaced at a second distance, the second distance being less than the first distance;
        wherein in the second position, a proximal portion of the primary struts define a generally circular mouth and the primary struts extend generally distally from the mouth to form a generally distally tapering filter body; and
        a plurality of secondary struts coupled to the shaft;
        wherein the secondary struts have a proximal end and a distal end;
        further wherein the primary struts and the secondary struts are differentiated by at least one of their points of coupling to the distal end of the shaft and their relative strut diameters.

2. An embolus extractor in accordance with claim 1, further comprising a sleeve slidably coupling the distal ends of the primary struts to the shaft.

3. An embolus extractor in accordance with claim 1, further comprising a sleeve slidably coupling the proximal ends of the primary struts to the shaft.

4. An embolus extractor in accordance with claim 1, wherein in the first position, the primary struts are disposed generally parallel to and adjacent the shaft.

5. An embolus extractor in accordance with claim 1, wherein the proximal portion of the primary struts forming the mouth extend from the shaft at between 45° to 90° the length of the shaft.

6. An embolus extractor in accordance with claim 1, wherein the proximal portions of the primary struts forming the mouth extend from the shaft at between 60° to 90° to the length of the shaft.

7. An embolus extractor in accordance with claim 1, wherein the proximal portions of the primary struts forming the mouth extend from the shaft at between 80° to 90° to the length of the shaft.

8. An embolus extractor in accordance with claim 1, wherein the proximal portion of the primary struts forming the mouth extends generally proximally from the shaft.

9. An embolus extractor in accordance with claim 1, wherein the proximal portion of the primary struts forming the mouth extends generally distally from the shaft.

10. An embolus extractor in accordance with claim 1, wherein the primary struts include a shape memory material.

11. An embolus extractor in accordance with claim 10, wherein the shape memory material includes a NiTi alloy.

12. An embolus extractor in accordance with claim 1, wherein the secondary struts have a transverse cross sectional area; wherein the primary struts each have a transverse cross sectional area greater than the transverse cross sectional area of the secondary struts.

13. An embolus extractor in accordance with claim 1, further comprising at least one sleeve slidably coupling the distal ends of the secondary struts to the shaft.

14. An embolus extractor in accordance with claim 1, further comprising at least one sleeve slidably coupling the proximal ends of the secondary struts to the shaft.

15. The embolus extractor in accordance with claim 1, wherein the secondary struts form at least a portion of a generally circular mouth.

16. The embolus extractor in accordance with claim 1, wherein at least one secondary strut is coupled to the shaft away from at least one primary strut.

17. The embolus extractor in accordance with claim 1, wherein at least one secondary strut extends from the shaft at a distance away from at least one primary strut.

18. The embolus extractor in accordance with claim 1, wherein the primary struts can move independently of at least one of the secondary struts.

19. The embolus extractor in accordance with claim 1, wherein at least one of the struts can rotate about the elongate shaft.

20. The embolus extractor in accordance with claim 1, wherein at least one of the struts can translate at least in part along the elongate shaft.

21. The embolus extractor in accordance with claim 1, wherein at least one strut includes a radiopaque material.

22. An embolus extractor, comprising:
    an elongate shaft having a proximal end and a distal end;
    a first strut having a proximal end and a distal end, the proximal end of the strut being coupled to the shaft;
    the strut having a first position and a second position, wherein in the first position, the distal end and the proximal end of the strut are spaced at a first distance, and in the second position, the distal end and the proximal end of the strut are spaced at a second distance being less than the first distance;
    wherein in the second position, a proximal portion of the first strut defines a generally circular mouth and the strut extends generally distally from the mouth to form a generally distally tapering filter body; and one or more additional struts coupled to the shaft, wherein at least one of the additional struts has a transverse cross-sectional area; wherein the first strut has a transverse cross-sectional area greater than the cross-sectional area of at least one of the additional struts.

23. An embolus extractor in accordance with claim 22, wherein in the first position, the strut is disposed generally parallel to the shaft.

24. An embolus extractor in accordance with claim 22, wherein the proximal portion of the strut forming the mouth, extends from the shaft at between 45° to 90° to the length of the shaft.

25. An embolus extractor in accordance with claim 22, wherein the proximal portion of the strut forming the mouth, extends from the shaft at between 60° to 90° to the length of the shaft.

26. An embolus extractor in accordance with claim 22, wherein the proximal portion of the strut forming the mouth, extends from the shaft at between 80° to 90° to the length of the shaft.

27. An embolus extractor in accordance with claim 22, wherein the strut includes a shape memory material.

28. An embolus extractor in accordance with claim 27, wherein the shape memory material includes a NiTi alloy.

29. An embolus extractor in accordance with claim 22, wherein at least one of the additional struts is coupled to the shaft away from the first strut.

30. An embolus extractor in accordance with claim 22, wherein at least one of the additional struts extends from the shaft at a distance away from the first strut.

* * * * *